United States Patent [19]

Westland et al.

[11] Patent Number: 5,362,713

[45] Date of Patent: Nov. 8, 1994

[54] DRILLING MUD COMPOSITIONS

[75] Inventors: John A. Westland, Bothell, Wash.; Glenn S. Penny, Duncan, Okla.; Deborah A. Lenk, Federal Way, Wash.

[73] Assignee: Weyerhaeuser Company, Tacoma, Wash.

[21] Appl. No.: 860,291

[22] Filed: Mar. 26, 1992

Related U.S. Application Data

[63] Continuation-in-part of Ser. No. 714,913, Jun. 13, 1991, abandoned, which is a continuation-in-part of Ser. No. 450,360, Dec. 13, 1989, Pat. No. 5,009,797.

[51] Int. Cl.$^5$ .............................................. C09K 7/02
[52] U.S. Cl. ................................. 507/110; 507/113; 507/114; 507/115; 507/120
[58] Field of Search .................... 252/8.551, 8.554; 166/273; 435/101; 507/110

[56] References Cited

U.S. PATENT DOCUMENTS

| | | | |
|---|---|---|---|
| 3,953,336 | 4/1972 | Daigle | 252/8.5 |
| 4,422,947 | 12/1983 | Dorsey et al. | 252/8.5 |
| 4,425,241 | 1/1984 | Swanson | 252/8.5 |
| 4,514,563 | 4/1985 | Fujiyama et al. | 435/101 X |
| 4,575,551 | 3/1986 | Fujiyama et al. | 435/101 X |
| 4,629,575 | 12/1986 | Weibel . | |
| 4,778,608 | 10/1988 | Alexander . | |
| 4,879,228 | 11/1989 | Mays et al. | 435/101 |
| 4,905,761 | 3/1990 | Bryant | 166/273 X |
| 5,009,797 | 4/1991 | Penny et al. | 252/8.551 |

FOREIGN PATENT DOCUMENTS

| | | |
|---|---|---|
| 0186495 | 7/1986 | European Pat. Off. . |
| 0228779 | 7/1987 | European Pat. Off. . |
| 61-113601 | 5/1986 | Japan . |
| 61-212295 | 9/1986 | Japan . |
| 61-221201 | 10/1986 | Japan . |
| 1570487 | 7/1980 | United Kingdom . |
| 2153834 | 8/1985 | United Kingdom . |
| 2244503 | 12/1991 | United Kingdom . |
| 8908148 | 9/1989 | WIPO . |
| 8911783 | 12/1989 | WIPO . |
| 8912107 | 12/1989 | WIPO . |

OTHER PUBLICATIONS

A. F. Turbak, et al., Microfibrillated Cellulose, A New Cellulose Product: Properties Uses and Commercial Potential, Journal of Applied Polymer Science Applied Polymer Symposium 37,815 (1983).
"Drilling and Workover/Completion Fluids", Oil Field Chemicals-Worldwide, Dec. 1988.
Abstract of a paper presented at the European Petroleum Conference, Oct. 17–19, 1988.
Brown, Jr. et al, *J. Applied Polymer Science,* vol. 37, pp. 33–78 (1983).

*Primary Examiner*—Gary Geist
*Attorney, Agent, or Firm*—Stoel Rives Boley Jones & Grey

[57] ABSTRACT

The addition of relatively small quantities of reticulated bacterial cellulose to well bore drilling muds improves their rheological properties. A preferred reticulated bacterial cellulose is one produced under agitated culture conditions using strains of a bacterium from the genus Acetobacter. Reticulated bacterial cellulose may be used in place of a conventional gellant or in combination with conventional gellants to provide improved drilling muds.

11 Claims, No Drawings

DRILLING MUD COMPOSITIONS

This application is a continuation-in-part of patent application Ser. No. 07/714,913, filed Jun. 13, 1991, now abandoned which is a continuation-in-part of International Patent Application No. PCT/US90/07318, filed on Dec. 11, 1990 which is a continuation-in-part of U.S. patent application Ser. No. 07/450,360, filed Dec. 13, 1989, now U.S. Pat. No. 5,009,797.

TECHNICAL FIELD

The present invention relates to drilling mud compositions and, in particular, to improved drilling mud compositions and methods for preparing and using drilling mud compositions containing an additive that confers improved rheological properties to the drilling mud.

BACKGROUND OF INVENTION

A drilling mud or fluid is typically pumped through a hollow drill stem and out an attached drill bit as an aid to drill rotation during the formation of a bore hole. In addition to rheological benefits, the drilling mud cools and lubricates the bit and stem, suspends drilling cuttings, and deposits a filter cake on the walls of the bore hole while transporting drilling cuttings upwardly to a settling pit on the surface. Removal of drilling cuttings from the borehole during drilling operations is essential. Drilling muds also typically function to prevent gases in a geological formation from escaping through bore hole walls, maintain bore hole stability, and protect formation productivity by preventing fluid loss.

Drilling muds may be characterized as: air-gas systems, including foam muds and aerated muds; oil-based systems, including invert-emulsion muds; and water-based systems, including bentonite muds, calcium muds, low-solids/nondispersed polymer muds, and salt muds.

Drilling muds contain a variety of components specifically selected for the depth, bore hole diameter, formation pressure, and structure of a particular well. These components generally include viscosifiers to enhance viscosity; fluid loss additives to prevent fluid penetration into formation reservoirs; weighting agents to consolidate drilling fragments and control formation pressures; dispersants to disperse solid matter; lost circulation materials to plug leaks in bore holes; shale controllers to prevent shale hydration and disintegration; emulsifiers and demulsifiers to improve bit efficiency; oil wetting agents and secondary emulsifiers to enhance fluid stability; and inorganic chemicals to adjust pH and supply proper ion concentrations. Other drilling mud components include torque reducing lubricants, foaming and defoaming agents, biocides, and corrosion inhibitors. A more detailed description of drilling muds can be found in Drilling Fluids Optimization: A Practical Field Approach by James L. Lummus and J. J. Azar.

Rheological control agents, and specifically viscosifiers, are among the most important drilling mud components because such agents permit the muds to function under diverse shear conditions. Drilling muds, for example, should ideally have low viscosity during mixing and pumping to minimize the energy input required during these operations. However, the viscosity should be sufficiently high during drilling so that drilling cuttings are maintained in suspension and carried out of the bore hole. Moreover, drilling muds must have sufficient gel strength to maintain cutting fragments in suspension during periods when drilling and pumping operations are stopped or the wellbore is highly deviated.

The hydrocarbon recovery industry preferably employs drilling muds that exhibit reduced viscosity as shear conditions increase. The relatively higher viscosity exhibited at lower shear conditions helps to maintain drilling cuttings in suspension toward the top of a bore hole, while lower viscosity exhibited under higher shear conditions improves drill bit lubrication, drilling mud flow rate, and drilling cutting distribution. High temperatures generated in proximity to the rotary drill bit also influence the rheological characteristics of drilling muds.

Drilling mud polymers are introduced is to provide enhanced viscosity and viscosity control, increased gel strength, and/or suspension and removal of drilling cuttings during drilling operations. Polymers used in drilling muds are usually based on water soluble derivatives of common polysaccharide materials such as xanthan, guar gum, other natural gums, cellulose ethers and esters, and bacterially produced water soluble polysaccharides. Xanthan is often used by the hydrocarbon recovery industry because it is very stable and functions as a fluid loss additive as well as a rheological control agent. Cellulose ethers and esters commonly employed as gellants include hydroxyethyl cellulose (HEC), carboxymethyl cellulose (CMC) carboxymethylhydroxyethyl cellulose (CMHEC), and hydroxypropylmethyl cellulose (HPMC). Additional polymers used include partially hydrolyzed polyacrylamides (PHPA), polyacrylamide/polyacrylate co-polymers, mixed metal hydroxides, and hydroxypropyl guar.

Well conditions, particularly well temperatures, have significant bearing on the choice of polymer. Drilling deeper wells that typically exhibit higher operating temperatures presents challenges and requires greater control over the rheological properties of drilling muds. Additionally, the composition of the make-up water can dramatically affect the properties of polymers used in drilling muds. Fresh, purified water is unavailable at many well sites. The presence of metal ions and varying salt concentrations may adversely affect how a particular polymer functions, particularly at high temperatures.

In general, increasing the polymer concentration in the drilling mud results in increased viscosity. Practical, economical, and operational considerations, however, limit the amount of polymer that can be introduced to a drilling mud to increase its viscosity. Additionally, excessive polymer loading may result in poor mixing efficiency and substantial frictional resistance.

The behavior of drilling muds is evaluated in terms of plastic viscosity, yield point, and gel strength. The plastic viscosity or shearing stress expresses the internal resistance to fluid flow resulting from the interaction of solids in the drilling mud. The yield point expresses the internal resistance of the mud to initial flow. The gel strength expresses the electrical attractive forces within the drilling mud under static conditions.

Although substantial research efforts have been devoted to developing stable and economically feasible drilling muds that exhibit the desired plastic viscosity, yield point, gel strength, and other rheological properties, the results have not been entirely satisfactory. The present invention is therefore directed to providing economically feasible drilling mud additives to produce drilling mud compositions that provide improved rheological properties and are stable throughout drilling operations.

SUMMARY OF THE INVENTION

Accordingly, it is an object of the present invention to provide novel drilling mud compositions exhibiting improved rheological properties, and to provide methods for making and using such compositions.

It is a further object of the present invention to provide drilling muds having increased stability and viscosity and, in general, exhibiting rheological properties that promote enhanced suspension and transport of drilling cuttings while cooling and lubricating the drill bit and drill stem.

It is another object of the present invention to provide drilling muds that contain an economically feasible additive that imparts stability to the mud.

It is still another object of the present invention to provide drilling muds having relatively low concentrations of polymer while maintaining desirable rheological properties.

Bacterial cellulose having a highly reticulated structure is used alone or in combination with other polymers in accordance with the present invention. The introduction of reticulated bacterial cellulose to drilling muds confers several advantageous properties. In particular, higher viscosities are achieved, without concomitant increases in friction under flow conditions. Additionally, drilling muds incorporating reticulated bacterial cellulose exhibit substantially improved suspension and transport of drill cuttings from the bottom of the wellbore to the surface, even at drilling mud viscosities equivalent to those achieved using only common polymers.

Reticulated bacterial cellulose may be incorporated in drilling muds comprising conventional polymers including xanthan, hydroxyethyl cellulose, carboxymethylhydroxyethyl cellulose, and carboxymethyl cellulose, hydroxypropyl cellulose, partially hydrolyzed polyacrylamides, and hydroxypropyl guar. Additionally, reticulated bacterial cellulose may be used in combination with microbially produced water soluble polysaccharides in drilling muds of the present invention.

Polymers according to the present invention are generally present in concentrations of about 1.4 to 8.6 g/L (0.5 to 3.0 lb/barrel) of mixed drilling mud, and more commonly in amounts of about 2.8 to 7.1 g/L drilling mud. The improvement observed and attributed to the introduction of reticulated bacterial cellulose requires relatively small amounts of bacterial cellulose, e.g., in the range of about 0.34 to 7.1 g/L of mixed drilling mud, and preferably in the range of about 1.1 to 4.3 g/L of mixed drilling mud. All concentrations recited herein are measured on a dry weight basis unless otherwise indicated.

Reticulated bacterial cellulose suitable for use in methods and compositions of the present invention includes cellulose produced by various species of Acetobacter organisms. Bacterial cellulose is distinguishable from plant cellulose in that it is a reticulated fibrillar material having a very small cross-sectional diameter and a high surface area. It has very different properties in this regard from purified, plant-derived cellulose, e.g., wood pulps. The bacterial cellulose preferred for use in the methods and compositions of the present invention is produced by a strain of the Acetobacter bacterium that is resistant to mutation to non-cellulose producing types and is cultured under agitated culture conditions.

The above-mentioned and additional features of the present invention and the manner of obtaining them will become apparent, and the invention will be best understood by reference to the following more detailed description.

DESCRIPTION OF THE PREFERRED EMBODIMENTS

Bacterial cellulose produced by microorganisms capable of producing cellulose, such as those of the genus Acetobacter, Pseudomonas, Agrobacterium, and the like may be employed according to methods of the present invention. Preferred bacterial cellulose is produced by a strain of Acetobacter bacterium cultured under agitated cell culture conditions. The term "reticulated bacterial cellulose," as used in the specification and claims herein, refers to cellulose produced by microorganisms using fermentation techniques that is characterized by a highly reticulated, branching interconnected network of fibers and that is insoluble in water.

Cellulose fibers produced by microorganisms, although chemically similar to cellulose derived from wood pulp, differ from plant-derived cellulose in a number of important respects. An important difference is that cellulose fibers produced by capable strains of Acetobacter under agitated cell culture conditions are about two orders of magnitude narrower than the cellulose fibers typically produced by pulping birch or pine wood. The small cross-sectional size of this bacterial cellulose and the concomitantly greater cross-sectional surface area provide important advantages in a variety of applications. In particular, its high surface area and hydrophilic properties enhance its ability to bind water. Reticulated bacterial cellulose produced by Acetobacter microorganisms under agitated cell culture conditions binds water at levels not even achieved by very highly refined plant celluloses.

The properties of highly reticulated bacterial cellulose produced using agitated cell culture conditions, as well as suitable bacterial strains and cell culture conditions are disclosed in European Patent Application 0 228 779, published Jul. 15, 1987, which is incorporated herein by reference in its entirety.

Growth and harvesting of bacterial cellulose produced under static conditions may be accomplished as described in *Methods in Carbohydrate Chemistry, Volume III—Cellulose*, R. L. Whistler, Ed., Chapter 2, Academic Press New York (1963). In preferred embodiments of the methods of the present invention, microbial cell growth is conducted under agitated culture conditions and, as a result, the microbially produced cellulose is characterized by a substantially continuous, reticulated network of fiber strands.

Bacterial cellulose according to a preferred embodiment of the present invention may be produced from a strain of Acetobacter aceti var. xylinum grown as a subculture of ATCC Accession No. 53524, deposited Jul. 25, 1986 under the terms of the Budapest Treaty. The bacteria may be cultured under conditions similar to those described below.

The base medium used for cell culture is referred to as R 70-3 medium. Suitable R 70-3 medium comprises:

| Ingredient | Final Conc. (mM) |
|---|---|
| $(NH_4)_2SO_4$ | 25 |
| $KH_2PO_4$ | 7.3 |
| Na Citrate | 4.0 |
| $MgSO_4$ | 1.0 |
| $FeCl_3$ | 0.05 |
| $CaCl_2$ | 0.10 |
| $Na_2MoO_4$ | 0.001 |
| $ZnSO_4$ | 0.005 |
| $MnSO_4$ | 0.005 |
| $CuSO_4$ | 0.001 |
| $CoCl_2$ | 0.001 |
| $NiCl_2$ | 0.001 |
| Vitamin mix | 10 mL/L |
| Carbon source | As later specified (usually glucose 2% or 4%, w/v) |
| Corn steep liquor (supernatant fraction after centrifugation) | As later specified (usually 1% to 4%, v/v) |
| Buffer 3,3 Dimethylglutaric acid (DMG) | 25 mM |

The final pH of the medium is 5.0, ±0.2.
A suitable vitamin mix may be formulated as follows:

| Ingredient | Conc. (Mg/L) |
|---|---|
| Inositol | 200 |
| Niacin | 40 |
| Pyridoxine HCl | 40 |
| Thiamine HCl | 40 |
| Ca Pantothenate | 40 |
| Riboflavin | 20 |
| p-Aminobenzoic acid | 20 |
| Folic acid | 0.2 |
| Biotin | 0.2 |

The carbon source generally comprises monosaccharides or mixtures thereof, such as glucose and fructose, disaccharides such as sucrose, and mixtures of mono- and disaccharides. The carbon source, typically glucose, is generally provided in concentrations of about 0.5% to about 7.0% (w/v), and preferably about 2.0%–4.0% (w/v).

Corn steep liquor, yeast extract, casein hydrolysate, ammonium salts or other nitrogen-rich substances may be used as a general source of nitrogen, amino acids, minerals and vitamins. Corn steep liquor is preferred, and suitable concentrations thereof range from about 0.1% to about 10% (v/v). Cell culture media comprising about 5% (v/v) corn steep liquor is preferred for shaking flask cultures. In fermenters, an initial concentration of corn steep liquor may be supplemented during the fermentation run with additional aliquots of corn steep liquor. Yeast extract may be employed in place of corn steep liquor as an additive to the culture medium. Yeast extract in a quantity of about 1% (v/v) is suitable and may be obtained from Universal Foods, Milwaukee, Wis., under the tradename Amberex 1003.

Corn steep liquor varies in composition, depending upon the supplier and mode of treatment. A product obtained as Lot E804 from Corn Products Unit, CPC North America, Stockton, Calif., may be considered typical and has a pH of about 4.5 and the following composition:

| Major Component | % |
|---|---|
| Solids | 43.8 |
| Crude protein | 18.4 |
| Fat | 0.5 |
| Crude fiber | 0.1 |
| Ash | 6.9 |
| Calcium | 0.02 |
| Phosphorous | 1.3 |
| Nitrogen-free extract | 17.8 |
| Non-protein nitrogen | 1.4 |
| NaCl | 0.5 |
| Potassium | 1.8 |
| Reducing sugars (as dextrose) | 2.9 |
| Starch | 1.6 |

Bacteria were first multiplied as a pre-seed culture using 4% (w/v) glucose as the carbon source and 5% (w/v) corn steep liquor. Cultures were grown in 100 mL of the medium in a 750 mL Falcon No. 3028 tissue culture flask at 30° C. for 48 hours. The entire contents of the culture flask were blended and used to make a 5% (v/v) inoculum of the seed culture. Preseeds were streaked on culture plates to monitor for homogeneity and contamination.

Seed cultures were grown in 400 mL of the above-described culture medium in 2 L baffled flasks in a reciprocal shaker at 125 rpm at 30° C. for two days. Seed cultures were blended and streaked as before to check for contamination before further use.

Bacterial cellulose was initially made in a continuously stirred 14 L Chemap fermenter using a 12 L culture volume inoculated with 5% (v/v) of the seed cultures. An initial glucose concentration of 32 g/L in the medium was supplemented during the 72-hour fermenter run with an additional 143 g/L added intermittently during the run. In similar fashion, the initial 2% (v/v) corn steep liquor concentration was augmented by the addition of an amount equivalent to 2% by volume of the initial volume at 32 hours and 59 hours. Cellulose concentration reached about 12.7 g/L during the fermentation. Throughout the fermentation, dissolved oxygen concentration was maintained at about 30% air saturation.

Following fermentation, cellulose was allowed to settle, and the supernatant liquid was poured off. The remaining cellulose was washed with deionized water and then extracted with 0.5M NaOH solution at 60° C. for two hours. After extraction, the cellulose was again washed with deionized water to remove residual alkali and bacterial cells. More recent experimental studies have shown that a 0.1M NaOH solution is entirely adequate for the extraction step. The purified microbially produced cellulose was maintained in wet condition for further use. This material was readily dispersible in water to form a uniform slurry. Bacterial cellulose for the later samples was made in 250 L and 6000 L fermenters.

The bacterial cellulose produced under stirred or agitated conditions, as described above, has a microstructure quite different from that of bacterial cellulose produced in conventional static cultures. It is a reticulated product formed by a substantially continuous network of branching, interconnected cellulose fibers. The bacterial cellulose prepared as described above by agitated fermentation has filament widths much smaller than softwood pulp fibers or cotton fibers. Typically, these filaments are about 0.1 to 0.2 microns in width with indefinite length due to the continuous network structure. A softwood fiber averages about 30 microns in width and 2 to 5 mm in length, while a cotton fiber is about half this width and about 25 mm long.

According to preferred embodiments of the present invention, cellulose-producing microorganisms of the genus Acetobacter are cultured under agitated conditions to produce bacterial cellulose characterized by a substantially continuous, reticulated network of fiber strands. Characteristics of cellulose-producing bacteria and preferred growth and agitated culture conditions are fully described in U.S. Pat. No. 4,863,565, entitled "Sheeted Products Formed From Reticulated Microbial Cellulose", which is herein incorporated by reference in its entirety.

Preferred drilling mud compositions, according to the present invention, can be classified generally as aqueous polymer systems. Drilling mud compositions of the present invention preferably have adequate viscosity to transport drilling cuttings out of the bore hole, and a low yield point so that pumping energies are kept to a minimum. Drilling mud compositions having a plastic viscosity of about 5 to 7 mPa.s and a yield point of about 0.63 to 0.76 Kg/m$^2$ are preferred.

Reticulated bacterial cellulose may be substituted for the polymer in drilling muds of the present invention. Alternatively, reticulated bacterial cellulose may be used as an additive in combination with conventional polymers to enhance the rheological properties of drilling muds. Utilization of reticulated cellulose alone, or as an additive to conventional polymers, provides a drilling mud system having improved rheological properties at a lower cost than would be required for conventional polymers to confer equivalent properties.

Reticulated bacterial cellulose may be used in combination with the following polymers to provide drilling muds having improved rheological properties: xanthan, hydroxyethyl cellulose, carboxymethyl hydroxyethyl cellulose, carboxymethyl cellulose, hydroxypropyl cellulose, partially hydrolyzed polyacrylamides, and hydroxypropyl guar. Additionally, reticulated bacterial cellulose may be used in combination with microbially produced water soluble polysaccharides in drilling muds. The term "microbially produced polysaccharides," as used in the specification and claims herein, refers to water soluble polysaccharides produced by microorganisms wherein a substantial portion of the main polymeric backbone comprises glucose molecules. Scleroglucan and succino-glycan are exemplary water soluble, microbially produced polysaccharides.

The concentrations of drilling mud constituents are expressed herein in terms of g/L, except where expressly noted otherwise. Preferred drilling mud compositions of the present invention preferably comprise from about 0.34 to about 7.1 g/L reticulated bacterial cellulose, and most preferably from about 1.0 to about 3.0 g/L reticulated bacterial cellulose. Where reticulated bacterial cellulose is utilized in combination with polymer, ratios of polymer:cellulose of from about 90:10 to about 10:90 are suitable, and ratios of from about 30:70 to about 70:30 are preferred. Other conventional drilling mud constituents, such as drill solids, bentonite, and soda ash are also preferably incorporated in the drilling muds of the present invention.

The following examples set forth specific drilling mud compositions and methods for their production and use for the purpose of more fully understanding preferred embodiments of the present invention, and are not intended to limit the invention in any way.

EXAMPLE I

Several drilling mud formulations were tested using a base mud composition of 14.3 g/L of Western or Wyoming bentonite, 28.5 g/L Texas Ball Clay (nonwetting) drill solids, and 0.71 g/L soda ash. The bentonite was prehydrated at 63 g/L for 24 hours before it was diluted to the concentration used, and the drill solids were added while the muds were circulating. Selected gellants were added to the base mud composition as follows: Sample 1–4.3 g/L xanthan; Sample 2–4.3 g/L HEC; and Sample 3–1:1 by weight blend of reticulated bacterial cellulose ("BAC") to HEC in total HEC/BAC drilling mud concentration of 4.3 g/L. The xanthan was fully hydrated before it was introduced to the mud. The polymer was blended, without shearing, with the bentonite before being introduced to the mud.

The drilling mud compositions were evaluated in a system designed to simulate drilling environments. The drilling muds were pumped through a coil of 1.3 cm (OD) tubing and then through a 0.3 cm orifice at a rate of approximately 23 liters per minute. This system resulted in a shear rate of about 1884 sec$^{-1}$ through the tubing and 145,000 sec$^{-1}$ through the orifice. Drilling muds were continuously circulated through this system and various rheological parameters, including plastic viscosity, yield point, and gel strength were measured at time intervals of up to 180 minutes. The measurements were performed in accordance with American Petroleum Institute procedure API RB 13B, eleventh edition, May 1985, using a Fann 35 viscometer. Results are shown below in Tables 1, 2 and 3.

TABLE 1

| | Plastic Viscosity, mPa · s | | |
|---|---|---|---|
| Time, Minutes | Sample 1 (xanthan) | Sample 2 (HEC) | Sample 3 (HEC/BAC, 1:1) |
| 0 | 8.0 | 11.0 | 10.0 |
| 30 | 5.0 | 12.0 | 8.0 |
| 60 | 5.5 | 12.0 | 9.0 |
| 90 | 5.0 | 8.0 | 8.0 |
| 120 | 5.0 | 5.0 | 7.0 |
| 150 | 5.0 | 5.0 | 6.0 |
| 210 | — | — | 5.0 |

TABLE 2

| | Yield Point, Kg/m$^2$ | | |
|---|---|---|---|
| Time, Minutes | Sample 1 (xanthan) | Sample 2 (HEC) | Sample 3 (HEC/BAC, 1:1) |
| 0 | 0.97 | 0.51 | 0.68 |
| 30 | 0.84 | 0.63 | 1.48 |
| 60 | 0.80 | 0.68 | 1.22 |
| 90 | 0.84 | 0.13 | 1.10 |
| 120 | 0.84 | 0.08 | 0.89 |
| 150 | 0.80 | 0.08 | 0.84 |
| 210 | — | — | 0.76 |

TABLE 3

| | Gel Strength, Kg/m$^2$ | | | | | |
|---|---|---|---|---|---|---|
| | Sample 1 (xanthan) | | Sample 2 (HEC) | | Sample 3 (HEC/BAC, 1:1) | |
| Time, Minutes | 10 sec | 10 min | 10 sec | 10 min | 10 sec | 10 min |
| 0 | 0.46 | 0.46 | 0.08 | 0.13 | 0.21 | 0.59 |
| 30 | 0.42 | 0.34 | 0.13 | 0.11 | 0.80 | 0.46 |
| 60 | 0.40 | 0.30 | 0.08 | 0.08 | 0.68 | 0.42 |
| 90 | 0.38 | 0.30 | 0.08 | 0.08 | 0.68 | 0.42 |
| 120 | 0.38 | 0.34 | 0.08 | 0.08 | 0.51 | 0.40 |

TABLE 3-continued

| | Gel Strength, Kg/m² | | | | | |
|---|---|---|---|---|---|---|
| Time, Minutes | Sample 1 (xanthan) | | Sample 2 (HEC) | | Sample 3 (HEC/BAC, 1:1) | |
| | 10 sec | 10 min | 10 sec | 10 min | 10 sec | 10 min |
| 150 | 0.34 | 0.30 | 0.08 | 0.08 | 0.46 | 0.38 |
| 210 | — | — | — | — | 0.46 | 0.38 |

With reference to Table 1, the drilling mud including xanthan as a polymer displays a relatively stable plastic viscosity of 5 mPa.s over time. The drilling mud incorporating HEC initially displays a higher than desirable plastic viscosity, but rapidly shears with time and temperature to a more desirable value. The drilling mud incorporating HEC/BAC displays a very stable plastic viscosity of 5 mPa.s over time. The performance of the HEC/BAC drilling mud is substantially equivalent or superior to the performance of the drilling mud incorporating xanthan, yet a HEC/BAC gellant can be provided at a much lower cost. The performance of the drilling mud incorporating HEC is less satisfactory.

The results shown in Table 2 demonstrate that the drilling mud incorporating xanthan displays a very stable yield point of about 0.8 Kg/m² over time. The drilling mud incorporating HEC initially displays a desirable yield point, but quickly shears out of the preferred range. The HEC/BAC drilling mud initially increases above the desirable yield point range but, then quickly stabilizes around a yield point value of 0.8 Kg/m².

The results shown in Table 3 demonstrate that the drilling mud incorporating xanthan exhibits stable gel strength and relatively strong gels for both 10 second and 10 minute tests. The HEC drilling mud exhibits poor gel strength and relatively fragile gels for both tests. The HEC/BAC drilling mud exhibits stable gel strengths and relatively strong gels for both tests.

The results shown in Tables 1–3 clearly demonstrate the advantages of adding BAC to a drilling mud in combination with another polymer. The addition of BAC produces a drilling mud composition that substantially mimics the performance of the substantially more expensive xanthan drilling mud. The estimated savings for substituting a 1:1 HEC/BAC drilling mud for a xanthan drilling mud is about 30–45%.

EXAMPLE II

Drilling mud base compositions were formulated as set forth in Example I. Polymers were added as follows: Sample 1–4.3 g/L partially hydrolyzed polyacrylic acid (PHPA) supplied from Aqualon (ASP 700) and Sample 2–3:1 mix of HEC/BAC with a total HEC/BAC drilling mud concentration of 4.3 g/L. The drilling mud compositions were tested to measure plastic viscosity, yield point and gel strength in accordance with the protocol set forth in Example 1, and the results are shown below in Tables 4, 5 and 6.

TABLE 4

| | Plastic Viscosity, mPa · s | |
|---|---|---|
| Time, Minutes | Sample 1 (PHPA) | Sample 2 (HEC/BAC, 3:1) |
| 0 | 10 | 10.0 |
| 30 | 8.5 | 8.0 |
| 60 | 8.5 | 8.0 |
| 90 | 9.0 | 7.0 |
| 120 | 8.8 | 6.0 |
| 150 | 7.5 | 5.0 |

TABLE 4-continued

| | Plastic Viscosity, mPa · s | |
|---|---|---|
| Time, Minutes | Sample 1 (PHPA) | Sample 2 (HEC/BAC, 3:1) |
| 180 | 8.0 | 4.0 |

TABLE 5

| Time, Minutes | Yield Point, Kg/m² | |
|---|---|---|
| | Sample 1 (PHPA) | Sample 2 (HEC/BAC, 3:1) |
| 0 | 0.34 | 0.59 |
| 30 | 0.34 | 1.01 |
| 60 | 0.34 | 0.89 |
| 90 | 0.25 | 0.76 |
| 120 | 0.21 | 0.68 |
| 150 | 0.22 | 0.68 |
| 180 | 0.17 | 0.63 |

TABLE 6

| | Gel Strength, Kg/m² | | | |
|---|---|---|---|---|
| Time, Minutes | Sample 1 (PHPA) | | Sample 2 (HEC/BAC, 3:1) | |
| | 10 sec | 10 min | 10 sec | 10 min |
| 0 | 0.08 | 0.06 | 0.21 | 0.38 |
| 30 | 0.04 | 0.21 | 0.42 | 0.51 |
| 60 | 0.08 | 0.40 | 0.76 | 0.42 |
| 90 | 0.13 | 0.38 | 0.93 | 0.46 |
| 120 | 0.08 | 0.38 | 0.68 | 0.44 |
| 150 | 0.08 | 0.38 | 0.59 | 0.40 |
| 180 | 0.06 | 0.36 | 0.42 | 0.38 |

With reference to Tables 4, 5 and 6, the drilling mud incorporating PHPA displays a higher than optimal plastic viscosity, a yield point well below the desirable range, and somewhat fragile gel strengths. The drilling mud incorporating a 3:1 ratio of HEC/BAC as a gellant, on the other hand, displays an initially high plastic viscosity which decreases to a suitable plastic viscosity after three hours, a yield point within the desirable range and gel strengths within the range where better suspensions of drilling cuttings occur. The results clearly demonstrate the advantages of adding BAC to a drilling mud in combination with a conventional polymer. The potential cost savings for substituting a 3:1 HEC/BAC drilling mud for a conventional polymer mud with substantially similar properties is about 60%. The HEC/BAC combination may also be used at lower concentrations and still maintain its efficacy. In addition, while it is necessary to add HEC or other polymers frequently to conventional drilling muds to maintain their plastic viscosities and yield points at suitable but not constant values, BAC can be added in much smaller amounts to muds of the present invention to maintain constant plastic viscosity and yield point values.

EXAMPLE III

Several drilling mud formulations were tested using a base mud having the following composition: 32 g Bentonite; 1.6 g carboxymethyl cellulose; and 1.1 L water. The Bentonite was mixed for 20 minutes with water using a paddle stirrer, the carboxymethyl cellulose was then added, and the base mud stirred for an additional 20 minutes using a paddle stirrer.

The test mud formulations were made to contain 0.8 ppb (pounds per barrel) of test polymer. The test polymers were BAC, xanthan and carboxymethyl cellulose (CMC). For each test mud 0.67 gm of test polymer was hydrated in 140 ml of distilled water. This was added to 140 ml of the base mud in a Waring blender and mixed for 15 minutes at 50% power. Samples of each mud were loaded onto a Fann 50 Viscometer with a computer data collection system (Bariod, Inc) using the B1 bob. Each sample was tested using a computer program that stepped the temperature. At each temperature plateau, a shear rate sweep from 3 to 600 rpm was conducted and parameters including the shear rate, shear stress, temperature and viscosity were measured and recorded. The apparent viscosity was then calculated at 40 sec$^{-1}$ at various temperatures. Results are shown below in Table 7.

TABLE 7

| Temperature, °F. | Drilling Mud Viscosity, (mPa · s) | | |
|---|---|---|---|
| | BAC | Xanthan | CMC |
| 80 | 536 | 302 | 312 |
| 100 | 570 | 422 | 272 |
| 150 | 459 | 308 | 186 |
| 200 | 365 | 215 | 124 |
| 250 | 300 | 73 | 79 |

These results demonstrate that the drilling mud containing BAC had a substantially higher viscosity than those containing xanthan or CMC over all temperature ranges tested. Moreover, the drilling mud containing BAC retained a much greater percentage of its viscosity with increasing temperatures.

EXAMPLE IV

Several drilling mud formulations were tested using the base mud described in Example III. The test formulations were made to contain 0.8 ppb of total test polymer. The test polymers used were xanthan and carboxymethyl cellulose, as well as one:one combinations of each of those polymers with BAC. For each test mud, 0.67 g of test polymer or polymer blend was hydrated in 140 ml of base mud in a Waring blender and mixed at 50% power for 15 minutes. Samples of each mud were loaded into a Fann 50 Viscometer with a computer data collection system (Bariod, Inc.) using the B1 bob. The temperature and shear rates were programmed as in the previous example. The apparent viscosity was then calculated at 40 sec$^{-1}$ for various temperatures. Results are shown below in Table 8.

TABLE 8

| Temperature, °F. | Drilling Mud Viscosity (mPa · s) | | | |
|---|---|---|---|---|
| | Xanthan | Xanthan/BAC | CMC | CMC/BAC |
| 80 | 302 | 365 | 312 | 520 |
| 100 | 422 | 358 | 272 | 468 |
| 150 | 308 | 259 | 186 | 327 |
| 200 | 215 | 215 | 124 | 261 |
| 250 | 73 | 229 | 79 | 216 |

These results demonstrate that drilling muds employing a combination of BAC with other polymers retain significantly more viscosity with increasing temperatures than those containing a conventional polymer alone. BAC in combination with other polymers may thus be expected to provide more stable and effective drilling mud performance across a wider spectrum of temperature ranges, and particularly at higher temperatures.

EXAMPLE V

Several drilling mud formulations were tested using a base mud having the following composition: 40 g Bentonite; 430.4 g NaCl; 4.0 g carboxymethyl cellulose; and 1.225 L water. The Bentonite was mixed for 30 minutes with water using a paddle stirrer, the salt was added and mixed an additional 60 minutes, and carboxymethyl cellulose was finally added and mixed for an additional 60 minutes.

The test mud formulations were made to contain 0.8 ppb (pounds per barrel) of BAC, xanthan and carboxymethyl cellulose (CMC) test polymer using the following process. For each test mud, 0.67 gm of the test polymer was hydrated in 140 ml of distilled water. This was added to 140 ml of the base mud in a Waring blender and mixed for 15 minutes at 50% power. Samples of each mud were loaded onto a Fann 50 Viscometer with a computer data collection system (Bariod, Inc.) using the B1 bob. Each sample was tested using a computer program that stepped the temperature. At each temperature plateau, a shear rate sweep from 3 to 600 rpm was conducted, and parameters including the shear rate, shear stress, temperature and viscosity were measured and recorded. The apparent viscosity was then calculated at 40 sec$^{-1}$ for each temperature. Results are shown below in Table 9.

TABLE 9

| Temperature, °F. | Drilling Mud Viscosity (mPa · s) | | |
|---|---|---|---|
| | BAC | Xanthan | CMC |
| 80 | 224 | 81 | 44 |
| 100 | 246 | 91 | 30 |
| 150 | 222 | 29 | 9 |
| 200 | 208 | 17 | 3 |
| 250 | 269 | 9 | 3 |

The results shown in Table 9 illustrate the dramatic effect salt concentrations can have on the viscosity of drilling muds. Fresh water is frequently unavailable at drilling sites and make-up water from a variety of local sources may be used. Conventional xanthan and CMC polymers were not effective in salt-containing drilling muds, while the performance of BAC in the same salt-containing drilling muds was far superior as evidenced by the significantly higher viscosities of drilling muds containing BAC at all temperature levels.

It will be readily apparent that many departures can be made from the embodiments shown in the examples while still remaining within the general scope of the invention. Thus, the invention should be considered as being limited only as it is defined in the following claims.

We claim:

1. A method of preparing a drilling mud composition for use during the formation of a bore hole comprising:
   providing an aqueous transport medium;
   dispersing sufficient amounts of a water insoluble reticulated bacterial cellulose in the medium to achieve a drilling mud having a plastic viscosity of at least about 5 cp; and
   adding one or more drilling mud constituents selected from the group consisting of drill solids, bentonite and soda ash to the medium.

2. A drilling mud composition comprising:
   an aqueous transport medium;
   a water insoluble reticulated bacterial cellulose dispersed in said medium to achieve a drilling mud having a plastic viscosity of at least about 5 cp; and one or more drilling mud constituents selected from the group consisting of drill solids, bentonite and soda ash.

3. A method of drilling a geological formation comprising:

rotating a hollow drill stem and attached drill bit within a geological formation to create a bore hole;

delivering a drilling mud through the drill stem and out of the drill bit at a sufficient volumetric rate and pressure to cause the drilling mud to rise between the drill stem and bore hole, the drilling mud comprising an aqueous transport medium and a sufficient amount of water insoluble reticulated bacterial cellulose dispersed in the medium to achieve a drilling mud having a plastic viscosity of at least about 5 cp.

4. The method of claim 1 in which the bacterial cellulose is produced by a cellulose generating strain of the genus Acetobacter grown under agitated cell culture conditions.

5. The method of claim 4 in which said Acetobacter strain is selected from one resistant to mutation to non-cellulose producing types under agitated cell culture conditions.

6. The method of claim 3 in which the water insoluble bacterial cellulose is present in an amount of about 0.3 to 7.0 g/L of drilling mud.

7. The method of claim 6 in which the water insoluble bacterial cellulose is present in an amount of about 1.0 to 3.0 g/L of drilling mud.

8. The method of claim 3 in which the drilling mud additionally comprises a water soluble polymer.

9. The method of claim 3 in which the water soluble polymer is selected from the group consisting of xanthan, hydroxyethyl cellulose, carboxymethyl hydroxyethyl cellulose, carboxymethyl cellulose, hydroxypropyl cellulose, partially hydrolyzed polyacrylamides, water soluble microbially produced polysaccharides, hydroxypropyl guar, and mixtures thereof.

10. The method of claim 3 in which the drilling mud additionally comprises one or more drilling mud constituents selected from the group consisting of drilling mud solids, bentonite and soda ash.

11. The method of claim 3 in which the drilling mud has a yield point of at least about 0.6 $Kg/m^2$.

* * * * *

UNITED STATES PATENT AND TRADEMARK OFFICE
CERTIFICATE OF CORRECTION

PATENT NO. : 5,362,713　　　　　　　　　　　　　Page 1 of 3

DATED : November 8, 1994

INVENTOR(S) : John A. Westland, et al.

It is certified that error appears in the above-identified patent and that said Letters Patent is hereby corrected as shown below:

Col. 3, line 7, change "t" in —theological— to "r".

Col. 3, line 33, add space between "well" and "bore".

Col. 3, line 40, delete space after "hydroxypropyl".

Col. 4, lines 47 & 64, change "Jul." to —July—.

Col. 4, line 53, delete space in "R. L.".

Col. 5, line 62, change "Wis." to "WI".

Col. 5, line 66, change "Calif." to "California".

Col. 6, lines 21 & 48, delete space after degree symbol and delete period in —C.—.

Col. 6, lines 48 & 52, add space before —M—.

Col. 7, line 24, change "mPa.s" to "cp".

Col. 7, lines 30 & 33, change "t" in "theological" to "r".

Col. 8, lines 37 & 9/61, in Table heading, add "#cp#" after "Viscosity,".

Col. 8, lines 37 & 9/61, put parentheses around "mPa.s".

Col. 9, lines 12 & 17, change "mPa.s" to "cp".

Col. 11, lines 16 & 48, delete "Drilling" before "Mud".

Col. 11, lines 16 & 48, add "Polymer" after "Mud".

UNITED STATES PATENT AND TRADEMARK OFFICE
CERTIFICATE OF CORRECTION

PATENT NO. : 5,362,713

DATED : November 8, 1994

INVENTOR(S) : John A. Westland, et al.

It is certified that error appears in the above-identified patent and that said Letters Patent is hereby corrected as shown below:

Col. 1, line 4, add "U.S." before --patent--.

Col. 1, lines 4 & 9, capitalize "p" in --patent--.

Col. 1, lines 5 & 9, capitalize "a" in --application--.

Col. 1, lines 5 & 9, delete "Ser.".

Col. 1, line 5, change "Jun." to --June--.

Col. 1, line 6, delete "now abandoned".

Col. 1, lines 8 & 9, change "Dec." to --December--.

Col. 1, line 10, change "Pat." to --Patent--.

Col. 1, line 28, add space between "bore" and "hole".

Col. 1, lines 55 & 56, underscore "Drilling Fluids Optimization: A Practical Field Approach".

Col. 1, line 56, delete space in "J. J."

Col. 2, line 2, add space between "well" and "bore".

Col. 2, line 10, add "s" to end of --cutting--.

Col. 2, line 14, delete "is".

Col. 2, line 32, delete hyphen in --co-polymers--.

UNITED STATES PATENT AND TRADEMARK OFFICE
CERTIFICATE OF CORRECTION

PATENT NO. : 5,362,713

DATED : November 8, 1994

INVENTOR(S) : John A. Westland, et al.

It is certified that error appears in the above-identified patent and that said Letters Patent is hereby corrected as shown below:

Col. 12, line 27, add comma after "Viscosity".

Col. 13, line 18, change "1" to "3".

Col. 14, line 11, change "3" to "8".

Signed and Sealed this

Eighteenth Day of April, 1995

*Attest:*

BRUCE LEHMAN

*Attesting Officer*    Commissioner of Patents and Trademarks